(12) United States Patent
Huber

(10) Patent No.: US 7,579,079 B2
(45) Date of Patent: Aug. 25, 2009

(54) UV-STABILISED PARTICLES

(75) Inventor: Adalbert Huber, Bensheim (DE)

(73) Assignee: Merck Patent GmbH, Darmstadt (DE)

( * ) Notice: Subject to any disclaimer, the term of this patent is extended or adjusted under 35 U.S.C. 154(b) by 186 days.

(21) Appl. No.: 10/518,464

(22) PCT Filed: Jun. 23, 2003

(86) PCT No.: PCT/EP03/06600

§ 371 (c)(1), (2), (4) Date: Oct. 18, 2005

(87) PCT Pub. No.: WO2004/029144

PCT Pub. Date: Apr. 8, 2004

(65) Prior Publication Data

US 2006/0155007 A1   Jul. 13, 2006

(30) Foreign Application Priority Data

Jun. 24, 2002   (DE) .................................. 102 28 186

(51) Int. Cl.
*B32B 5/66* (2006.01)

(52) U.S. Cl. ................ 428/403; 428/404; 428/405; 428/406; 428/407; 106/415; 106/418; 106/430; 106/435; 106/481; 106/499

(58) Field of Classification Search ............... 428/402, 428/403–407; 106/415, 418, 430, 435, 481, 106/499

See application file for complete search history.

(56) References Cited

U.S. PATENT DOCUMENTS

| | | | | |
|---|---|---|---|---|
| 5,563,242 A | * | 10/1996 | Winter et al. | ............ 524/91 |
| 6,176,918 B1 | * | 1/2001 | Glausch et al. | ............ 106/415 |
| 6,686,046 B2 | * | 2/2004 | Schauer et al. | ............ 428/403 |

FOREIGN PATENT DOCUMENTS

| | | |
|---|---|---|
| JP | 9047215 | 11/1997 |
| JP | 5239352 | 3/1998 |

OTHER PUBLICATIONS

Database WPI Section Ch, Week 199717 Derwent Publications Ltd., London, GB: AN 1997-186921 XP002259724.

Database WPI Section Ch, Week 199342 Derwent Publications Ltd., London, GB; AN 1993-331582 XP002259725.

* cited by examiner

*Primary Examiner*—Leszek Kiliman

(57) ABSTRACT

The present invention relates to UV-stabilised particles which are distinguished by the fact that they reflect or absorb light having wavelengths of from 290 to 500 nm. The invention furthermore relates to a process for the production of the particles according to the invention and to the use thereof in surface coatings, water-borne coatings, powder coatings, paints, printing inks, security printing inks, plastics, concrete, in cosmetic formulations, in agricultural sheeting and tent awnings, for the laser marking of papers and plastics, as light protection, and for the preparation of pigment compositions and dry preparations.

16 Claims, No Drawings

UV-STABILISED PARTICLES

The present invention relates to UV-stabilised particles which are distinguished by the fact that they reflect or absorb light having wavelengths of from 290 to 500 nm.

Surface coatings are generally provided with a UV filter, which is added to the coating in the form of a powder or liquid. In the case of plastics or powder coatings, the protection is effected by addition of these filters to the batch to be extruded. It is frequently advisable additionally to add a tertiary amine, such as, for example, 2,2,6,6 tetramethylpiperidine, to the surface coatings or powder coatings. The UV protection of surface coatings, powder coatings or plastics is frequently also necessary since the pigments or particles present therein have inadequate UV stability. For example, greying occurs on irradiation of BiOCl pigments with light, in particular UV light. BiOCl pigments in a solution or in the form of a composition are therefore generally offered with a UV absorber. However, solutions or compositions of this type have the disadvantage that the UV absorber has to be employed in relatively high concentrations relative to the pigment, which results in diverse defects in the application media.

The object of the present invention is therefore to provide UV-stabilised particles which can be incorporated into the application media easily and without problems and at the same time can be produced in a simple manner.

Surprisingly, it has now been found that the light stability of particles, such as, for example, BiOCl, can be greatly increased if the surface of these particles is coated directly with a UV stabiliser. The UV absorber here should reflect or absorb light having wavelengths of from 250 to 500 nm. The application and immobilisation of UV stabilisers to/on the particle surface results in significantly greater efficiency of the UV protection compared with a mixture consisting of particles and UV stabiliser. At the same time, the direct UV protection agent/particle surface contact results in a significantly lower concentration of the UV protection agent compared with direct use in surface coatings, powder coatings and plastics. Furthermore, diffusion of the UV protection agent in the application medium, which is the cause of diverse defects in surface coatings, powder coatings and plastics, is suppressed. The UV-resistant particles can, in contrast to the prior art, be employed in pure pulverulent form in the application media and not as a solution or composition.

The invention thus relates to UV-stabilised particles which are distinguished by the fact that they reflect or absorb light having wavelengths of from 290 to 500 nm.

The invention furthermore relates to the production of the particles according to the invention and to the use thereof, inter alia, in surface coatings, water-borne coatings, powder coatings, paints, printing inks, security printing inks, plastics and in cosmetic formulations. The particles according to the invention are furthermore also suitable for the preparation of pigment compositions and for the preparation of dry preparations.

All UV light-sensitive organic or inorganic particles known to the person skilled in the art can be stabilised by the process according to the invention. The particles may be spherical, needle-shaped or flake-form. The size of the particles is not crucial per se and can be matched to the particular application. In general, spherical particles have a diameter of 0.02-100 µm, particularly 0.03-20 µm and in particular 0.05-1 µm. Needle-shaped particles have a length of 0.05-10 µm, preferably 0.05-5 µm, in particular 0.05-1 µm. The particularly preferred substrates are flake-form substrates. Suitable flake-form substrates have a thickness of between 0.02 and 5 µm, in particular between 0.1 and 4.5 µm. The extension in the two other ranges is usually between 1 and 500 µm, preferably between 2 and 200 µm, and in particular between 5 and 60 µm.

Suitable particles are inorganic and organic pigments as well as mixtures thereof.

Suitable inorganic particles are, for example, $SiO_2$ beads which are uncoated or coated with one or more metal oxides or are fillers, fluorescent pigments, white pigments, such as, for example, titanium dioxide, zinc white, paint-grade zinc oxide, lead white, zinc sulphide, lithopone, black pigments, such as, for example, iron-manganese black, spinel black and iron oxide black, coloured pigments, such as, for example, chromium oxide, chromium oxide hydrate green, chromium green, cobalt green, ultramarine green, cobalt blue, ultramarine blue, iron blue, manganese blue, ultramarine violet, cobalt and manganese violet, iron oxide red, cadmium sulfoselenide, molybdate red, ultramarine red, iron oxide brown, mixed brown, spinel and corundum phases, chromium orange, iron oxide yellow, nickel-titanium yellow, chromium-titanium yellow, cadmium-zinc sulfide, chromium yellow, zinc yellow, alkaline earth metal chromates, Naples yellow and bismuth vanadate, magnetic pigments, such as, for example, $CrO_2$, $Fe_2O_3$, $Fe_3O_4$, Co-modified iron oxides, Ba ferrites and pure iron pigments, graphite flakes, effect pigments, holographic pigments and BiOCl.

The effect pigments used are preferably commercially available metal-effect pigments, such as, for example, ChromaFlair pigments from Flex, coated or uncoated aluminium flakes, gold-bronze pigments, for example from Eckart, coated iron oxide flakes, such as, for example, Paliochrom® pigments from BASF, Sicopearl pigments from BASF and goniochromatic pigments from BASF, as described, for example, in EP 0 753 545 A2, as well as pearlescent pigments and interference pigments—metal oxide—coated mica flake pigments—obtainable, for example, from Merck, Darmstadt, under the trade name Iriodin®. The latter are, for example, disclosed in the German Patents and Patent Applications 14 67 468, 19 59 998, 20 09 566, 22 14 545, 22 15 191, 22 44 298, 23 13 331, 25 22 572, 31 37 808, 31 37 809, 31 51 343, 31 51 354, 31 51 355, 32 11 602, 32 35 017, DE 38 42 330, DE 41 37 764, EP 0 608 388, DE 196 14 637, DE 196 18 569. Preference is given to the use of pearlescent pigments. In particular, $TiO_2$- and/or $Fe_2O_3$-coated mica pigments, $SiO_2$ flakes, $Al_2O_3$ flakes, glass flakes, ceramic flakes or synthetic support-free flakes are employed.

Particularly preferred inorganic pigments are BiOCl flakes, $TiO_2$ particles, fluorescent pigments, holographic pigments, conductive and magnetic pigments, metal-effect pigments, for example based on aluminium flakes, and effect pigments, such as, for example, pearlescent pigments, interference pigments, goniochromatic pigments, multilayered pigments based on flake-form substrates, such as, for example, natural or synthetic mica, $Al_2O_3$, $TiO_2$, $SiO_2$, $Fe_2O_3$, glass or graphite flakes. Preferred effect pigments are substrates coated with $TiO_2$ (rutile or anatase), such as, for example, $TiO_2$-coated natural or synthetic mica, $TiO_2$-coated $SiO_2$, $Al_2O_3$, graphite, glass, $Fe_2O_3$ or metal flakes, in particular aluminium flakes. Preference is furthermore given to multilayered pigments having two, three or more layers which contain one or more $TiO_2$ layers, and spherical $SiO_2$ particles, which may be coated with one or more metal oxides.

Suitable organic pigments from the Colour Index list are, for example, monoazo pigments C.I. Pigment Brown 25, C.I. Pigment Orange 5, 13, 36, 67, C.I. Pigment Red 1, 2, 3, 5, 8, 9, 12, 17, 22, 23, 31, 48: 1, 48: 2, 48: 3, 48: 4, 49, 49: 1, 52: 1, 52: 2, 53, 53: 1, 53: 3, 57: 1, 251, 112, 146, 170, 184, 210, and 245, C.I. Pigment Yellow 1, 3, 73, 65, 97, 151 and 183; diazo pigments C.I. Pigment Orange 16, 34 and 44, C.I. Pigment Red 144, 166, 214 and 242, C.I. Pigment Yellow 12, 13, 14, 16, 17, 81, 106, 113, 126, 127, 155, 174, 176 and 188; anthanthrone pigments C.I. Pigment Red 168, anthraquinone pigments C.I. Pigment Yellow 147 and 177, C.I. Pigment Violet 31; anthrapyrimidine pigments C.I. Pigment Red 122, 202 and 206, C.I. Pigment Violet 19; quinophthalone pigments C.I. Pigment Yellow 138; dioxazine pigments C.I. Pigment Yellow 138; dioxazine pigments C.I. Pigment Violet 23 and 37; flavanthrone pigments C.I. Pigment Blue 60 and 64; isoindoline pigments C.I. Pigment Orange 69, C.I. Pigment Red 260, C.I. Pigment Yellow 139 and 185; isoindolinone pigments C.I. Pigment Orange 61, C.I. Pigment Red 257 and 260, C.I. Pigment Yellow 109, 110, 173 and 185; isoviolanthrone pigments C.I. Pigment Violet 31, metal-complex pigments C.I. Pigment Yellow 117 and 153, C.I. Pigment Green 8; perinone pigments C.I. Pigment Orange 43, C.I. Pigment Red 194; perylene pigments C.I. Pigment Black 31 and 32, C.I. Pigment Red 123, 149, 178, 17j9, 190 and 224, C.I. Pigment Violet 29; phthalocyanine pigments C.I. Pigment Blue 15, 15: 1, 15: 2, 15: 3, 15: 4, 15: 6 and 16, C.I. Pigment Green 7 and 36; pyranthrone pigments C.I. Pigment Orange 51, C.I. Pigment Red 216; thioindigo pigments C.I. Pigment Red 88 and 181, C.I. Pigment Violet 38; triarylcarbonium pigments C.I. Pigment Blue 1, 61 and 62, C.I. Pigment Green 1, C.I. Pigment Red 81, 81: 1 and 169, C.I. Pigment Violet 1, 2, 3 and 27; Aniline Black (C.I. Pigment Black 1); Aldazine Yellow (C.I. Pigment Yellow 101) as well as C.I. Pigment Brown 22 and liquid crystal polymers (LCP pigments).

Particularly preferred organic pigments are azo pigments, liquid crystal polymers and fluorescent pigments.

It is also possible for mixtures of different particles/pigments to be stabilised by the process according to the invention.

The UV resistance of the above-mentioned particles is significantly increased by application of UV protection agents or UV stabilisers to the particle surface. The fixing of the UV protection agents/stabilisers to the particle surface is preferably achieved by applying the protection agent to the surface in combination with a polymer or polymer mixture.

The proportion of UV protection agent/stabiliser on the particle surface is dependent on the particle to be protected. The particles preferably comprise from 0.001 to 1000% by weight, particularly preferably from 0.01 to 500% by weight and in particular from 0.1 to 100% by weight, based on the particles.

The BiOCl flakes according to the invention comprise, for example, from 5 to 70% by weight, in particular from 10 to 50% by weight, of UV stabiliser on the surface.

Suitable UV stabilisers are known to the person skilled in the art and are commercially available, such as, for example, UV absorbers, UV reflectors, UV scattering agents, antioxidants, dyes, carbon-black particles, free-radical scavengers, microtitanium.

Suitable UV absorbers are, for example, benzotriazoles, triazines, oxanilides, benzophenones, arylated cyanoacrylates, in particular hydroxy-benzotriazoles, such as 2-(3',5'-bis(1,1-dimethylbenzyl)-2'-hydroxy-phenyl)benzotriazole, 2-(2'-hydroxy-5'-(tert-octyl)phenyl)benzotriazole, 2-(2'-hydroxy-3'-(2-butyl)-5'-(tert-butyl)phenyl)benzotriazole, bis (3-2H-benzotriazolyl)-2-hydroxy-5-tert-octyl)methane, 2-(4-hexoxy-2-hydroxy-phenyl)-4,6-diphenyl-1,3,5-triazine, and the benzophenone 2,4-dihydroxy-benzophenone.

Suitable UV absorbers are furthermore carbon black and UV scattering agents, such as, for example, cyanaralic acid derivatives.

UV protection agents which can be employed are likewise free-radical scavengers. Suitable free-radical scavengers are, for example, organic and inorganic nitro compounds, phenols, such as, for example, hydroquinones, fused aromatic compounds, hindered amines (HALS).

Particularly suitable UV-reflective protection agents are metals, nanoparticles, for example of titanium dioxide or iron oxide, titanium dioxide and barium sulfate. The term nanoparticles here is taken to mean organic, inorganic, metallic particles having a size of <300 nm, preferably <150 nm.

It is furthermore also possible to employ mixtures of different UV protection agents, with no limits being set on the mixing ratio. Particular preference is given to mixtures consisting of free-radical scavengers and carbon-black particles.

Particularly preferred UV stabilisers are 2-hydroxybenzophenones, 2-hydroxyphenylbenzotriazoles, 2-hydroxyphenyltriazines, oxanilides, triazoles, triazines, titanium dioxide nanoparticles, iron oxide nanoparticles, carbon black, hindered amines (HALS) and mixtures of the said UV stabilisers.

It is also possible for a UV protection agent to be copolymerised in order to prevent absorption through the skin, which is particularly desirable in the case of cosmetic products.

The particles according to the invention can be produced easily. The fixing of the UV protection agent to the particle surface to be protected is carried out by prior or simultaneous precipitation of a suitable polymer or, if the protection agent itself is a polymer, by precipitation thereof alone.

A particularly preferred process is fixing of the UV protection agents to the particle surface with LCST and/or UCST polymers.

LCST polymers and UCST polymers are polymers which are soluble in a solvent at low or elevated temperatures and are deposited from the solution as a separate phase on increasing or lowering the temperature and reaching the so-called LCST or UCST (lower or upper critical solution temperature respectively). Polymers of this type are described, for example, in the literature in "Polymere" [Polymers], H.-G. Elias, Hüthig und Wepf-Verlag, Zug, 1996, on pages 183 ff.

Suitable LCST polymers for the present invention are, for example, those as described in WO 01/60926 A1.

Particularly suitable LCST polymers are polyethylene oxide (PEO) derivatives, polypropylene oxide (PPO) derivatives, in particular acrylate-modified PEO-PPO-PEO three-block copolymers, polymethyl vinyl ether, poly-N-vinylcaprolactam, ethylhydroxyethylcellulose, poly-N-isopropylacrylamide and olefinic siloxane polymers.

Suitable UCST polymers are, in particular, polystyrene, polystyrene copolymers and polyethylene oxide copolymers.

The polymer content, based on the end product, is 0.1-80% by weight, preferably 1-30% by weight, in particular 1-20% by weight.

The UV protection agents or mixtures thereof are either applied directly to the surface to be protected and immobilised with LCST and/or UCST polymers or applied to the surface and immobilised in one step in the form of a mixture with LCST and/or UCST polymers.

The UV protection agent is preferably mixed with an immobilisable polymer or polymer mixture, preferably an LCST and/or UCST polymer, if desired in the presence of a solvent. The LCST polymer/protection agent mixture is dissolved at the temperature below the LCST, while the UCST polymer/protection agent solution is dissolved above the UCST. In general, the LCST temperature is 0.5-90° C., preferably 35-80° C., while the UCST temperature is 5-90° C., in particular 35-60° C. The particles to be stabilised are then added. The temperature is subsequently increased, in general by about 5° C. above the LCST or below the UCST, during which the polymer precipitates with the UV protection agent and deposits on the particle surface. Finally, the immobilisation takes place in the form of cross-linking of the polymer on the particle surface, with the polymer being fixed irreversibly to the particle surface. The immobilisation can take place by means of free radicals, cationically, anionically or by a condensation reaction. The LCST or UCST polymers are preferably crosslinked by means of free radicals or by a condensation reaction.

For free-radical crosslinking (immobilisation) of the deposited layer in water, use is preferably made of potassium peroxodisulfate or ammonium peroxodisulfate in concentration ranges of 1-100% by weight, based on the olefinic LCST or UCST polymer used for the coating. The crosslinking is carried out, depending on the LCST or UCST temperature of the polymer, at 0-35° C. using a catalyst, such as, for example, an Fe(II) salt, or at 40-100° C. by direct thermal decomposition of the free-radical initiator.

The particles are preferably admixed with the solution of the LCST or UCST polymer in the form of a dispersion, with the same solvent as that of the polymer solution preferably being used and the temperature of the dispersion being reduced to below the LCST or UCST. However, direct dispersal of the particles in the LCST or UCST solution can also take place.

If a solvent is required in the process according to the invention, the choice of solvent depends on the solubility of the polymer used. The solvent is preferably water or a water-miscible organic solvent. Water-miscible solvents also include solvents which have a miscibility gap with water. In these cases, the mixing ratios are selected in such a way that miscibility occurs. Examples of suitable solvents are mono- and polyalcohols, such as, for example, methanol, ethanol, n-propanol, isopropanol, glycol, glycerol, propylene glycol, polyethylene glycol, polybutylene glycol and the mono- and diethers of polyalkylene glycols with methanol, ethanol, propanol and butanol; ethers, such as, for example, tetrahydrofuran, dioxane, 1,2-propanediol propyl ether, 1,2-butane-1-methyl ether, ethylene glycol monomethyl ether, diethylene glycol monomethyl ether; esters, such as, for example, methyl acetate, monoesters of ethylene glycol or propylene glycols with acetic acid, butyrolactone; ketones, such as acetone or methyl ethyl ketone; amides, such as formamide, dimethylformamide, dimethylacetamide, N-methylpyrrolidone and hexamethylphosphoric triamide; sulfoxides and sulfones, such as, for example, dimethyl sulfoxide and sulfolane, alkanecarboxylic acid, such as formic acid or acetic acid.

Suitable solvents are, in particular, water, furthermore organic solvents, such as, for example, alcohols and glycols.

The LCST and/or UCST polymer coatings are particularly preferably carried out as complete sheathing of the particles.

The aftertreatment according to the invention further increases the chemical stability of the particles and at the same time simplifies handling of the particles, in particular incorporation into various application media. The particles according to the invention have increased stability to flocculation in water-borne coatings and to the formation of structures in the case of organic coating systems.

The UV-stabilised particles furthermore exhibit very good weather stability, very good dispersion behaviour and, owing to their stability, are very suitable for a very wide variety of application systems, in particular for waterborne and organic coatings.

The UV-stabilised particles are compatible with a multiplicity of colour systems, preferably from the area of surface coatings, water-borne coatings, powder coatings, paints, printing inks, security printing inks, plastics and cosmetic formulations. The particles according to the invention are furthermore also suitable for the laser marking of papers and plastics, as light protection, for colouring concrete and for applications in the agricultural sector, for example for greenhouse sheeting, and, for example, for colouring tent awnings.

It goes without saying that the particles according to the invention can also advantageously be used for various applications in the form of a blend with organic dyes, organic pigments or other pigments, such as, for example, transparent and opaque white, coloured and black pigments, and with flake-form iron oxides, organic pigments, holographic pigments, LCPs (liquid crystal polymers), and conventional transparent, coloured and black lustre pigments based on metal oxide-coated mica, glass, $Al_2O_3$, graphite and $SiO_2$ flakes, etc. The particles stabilised in accordance with the invention can be mixed in any ratio with commercially available pigments and fillers.

The particles according to the invention are furthermore suitable for the preparation of flowable pigment compositions and dry preparations, such as, for example, granules, briquettes, sausages, pellets, etc. The pigment composition and dry preparations are distinguished by the fact that they comprise at least one or more particles according to the invention, binders and optionally one or more additives.

The invention also relates to the use of the UV-stabilised particles in surface coatings, water-borne coatings, powder coatings, paints, printing inks, security printing inks, plastics, concrete, furthermore in cosmetic formulations, for the laser marking of papers and plastics, as pigments in corrosion protection, in agricultural sheeting and tent awnings and for the preparation of pigment compositions and dry preparations.

The invention thus also relates to formulations which comprise the pigment preparation according to the invention.

The following examples are intended to explain the invention in greater detail, but without limiting it.

EXAMPLES

Example 1

Example 1a

UV Stabilisation of BiOCl Pigments 0.25 g of benzotriazole derivative (UV absorber from Ciba-Geigy) are mixed with 1.0 g of modified LCST polymer (three-block copolymer based on polypropylene oxide, polyethylene oxide) and dissolved in 20 ml of distilled water at 23° C. 20 g of Bi-Flair® 83S paste (flake-form BiOCl pigment having a particle size of from 10 to 30 µm in dispersion, product from Merck KGaA, Germany) are subsequently stirred in in a dissolver at 200 rpm. The mixture is stirred at 23° C. for 5 minutes and warmed to 40° C. After the mixture has been stirred at 40° C. for a further 10 minutes, 1.0 g of potassium peroxodisulfate are added, and the mixture is warmed to 65° C. and crosslinked over the course of 2 h. The mixture is cooled to room temperature, 20 ml of water are added, and the pigments are separated from the liquid by centrifugation. The UV-stabilised pigments are washed with water and centrifuged off. Sufficient water is then added to the resultant pigment cake until the solids concentration in the pigment paste is about 50%.

Example 1b

Preparation of a Pigmented Water-Borne Coating

In each case, a water-borne coating pigmented with the UV-stabilised BiOCl pigments from Example 1a and with untreated BiOCl pigments is prepared by stirring 5 g of pigment paste (corresponds to 2.5 g of pigment) into 15 g of an acrylate/melamine-based water-borne coating. The water-borne coating is composed of

| | |
|---|---|
| 147.2 g | of Viacryl SC 323 w/70SBB, Vianova |
| 49.1 g | of Maprenal MF 501w/63EDGM, Clariant |
| 14.3 g | of triethylamine |
| 489.4 g | of dist. water |

Example 1c

Colour Measurements

The substrates used for the variously pigmented coating samples are glass specimen slides. The dry layer thickness of the opaque coating layers applied to the glass specimen slides is 100 μm after a 0.5 h long baking operation in a fan-assisted oven at 125° C.

The UV exposure is carried out in the Xenotest for a duration of 24 and 45 h. Damage to the pigment is determined colorimetrically by measuring the change in the lightness value L*. The colour measurements are carried out using the 45° measurement geometry and a Datacolor instrument. The results of the colour measurements are shown in Table 1.

TABLE 1

Drop in the L* value in % for the coating samples after UV exposure for 24 and 45 h:

| Experiment | Pigmented coating layer | 24 h | 45 h |
|---|---|---|---|
| No. 1 | Coating layer pigmented with BiOCl pigments | −17.0% | −25.0% |
| No. 2 | Coating layer pigmented with BiOCl pigments, UV protection in the coating | −7.0% | −10.0% |
| No. 3 | Coating layer pigmented with UV-stabilised BiOCl pigments according to Example 1 | −2.5% | −3.0% |

Investigation of the UV resistance of BiOCl pigments in water-borne coatings clearly shows that a considerable improvement in the UV resistance is achieved by means of a coating comprising UV protection agents using LCST polymers.

Example 2

Example 2a

UV Stabilisation of BiOCl Pigments with Carbon Black 0.1 g of carbon black (Special Black 350, Degussa-Huls AG) are mixed with 2.0 g of modified LCST polymer (polypropylene oxide diacrylate). The mixture is subsequently dispersed for 0.5 h in a Scandex, and 40 ml of dist. water are added. The resultant pigment composition is shaken briefly, and 20 ml are withdrawn, cooled to 0.5° C. and stirred in a dissolver until a homogeneous mixture has formed. 20 g of Bi-Flair® 83S paste are then stirred into the mixture. The mixture is stirred at 0.5° C. for 15 minutes and warmed to 23° C. After the mixture has been stirred for a further hour, 1 g of an acrylate-modified PEO-PPO-PEO polymer dissolved in 20 ml of distilled water is added, and the mixture is warmed to 50° C. 0.3 g of potassium peroxydisulfate in 10 ml of water is then added. The mixture is warmed to 65° C. and crosslinked at this temperature for a duration of 2 h. After the mixture has been cooled to room temperature, 20 ml of water are added, and the pigments are separated off from the liquid by centrifugation. The stabilised pigments are washed with water and centrifuged off. Sufficient water is then added to the pigment cake obtained by centrifugation until the solids concentration is about 50%.

Example 2b

Preparation of a Pigmented Water-Borne Coating

Pigmented water-borne coatings are prepared analogously to Example 1b by stirring 5 g of pigment paste (corresponding to 2.5 g of pigment) into 15 g of an acrylate/melamine-based water-borne coating.

Example 2c

Colour Measurements

The colour change of the carbon black-stabilised BiOCl pigments is compared with unmodified pigments in the respective coating layer. The results of the colour measurements are shown in Table 2.

TABLE 2

Drop in the L* value in % for the coating samples after UV exposure for 12 h:

| Experiment | Pigmented coating layer | 12 h |
|---|---|---|
| No. 1 | Coating layer pigmented with BiOCl pigments | −14.7% |
| No. 2 | Coating layer pigmented with UV-stabilised BiOCl pigments according to Example 2 | −6.3% |

The carbon black-stabilised BiOCl pigments exhibit significantly greater UV resistance compared with the unstabilised BiOCl pigments.

The invention claimed is:

1. UV-stabilised particles, comprising inorganic particles and one or more UV protection agents or UV stabilisers,
   wherein the inorganic particles are sheathed on the surface with a polymer layer of immobilisable polymer or polymer mixture and the polymer layer comprises or includes the one or more UV protection agents or UV stabilisers; and
   wherein the particles reflect or absorb light having wavelengths of from 290 to 500 nm.

2. UV-stabilised particles according to claim 1, wherein the UV protection agent or the UV stabiliser is selected from the group consisting of UV absorbers, UV reflectors, UV scattering agents, antioxidants, dyes, carbon-black particles, free-radical scavengers, microtitanium and mixtures thereof.

3. UV-stabilised particles according to claim 2, wherein the UV protection agent or the UV stabiliser is selected from the group consisting of benzophenones, triazoles, triazines, titanium dioxide nanoparticles, iron oxide nanoparticles, carbon black, hindered amines (HALS) and mixtures thereof.

4. UV-stabilised particles according to claim 1, wherein the particles comprise from 0.001 to 1000% by weight of UV protection agent or UV stabiliser, based on the total particle weight.

5. UV-stabilised particles according to claim 1, wherein the polymer is applied to the inorganic particle surface by precipitation in water and/or an organic solvent.

6. UV-stabilised particles according to claim 1, wherein the inorganic particles are platelet-shaped, spherical or needle-shaped.

7. UV-stabilised particles according to claim 1, wherein the inorganic particles are selected from the group consisting of BiOCl platelets, $TiO_2$ particles, fluorescent pigments, holographic pigments, pearlescent pigments, interference pigments, multilayered pigments, metal-effect pigments, goniochromatic pigments, and conductive and magnetic pigments.

8. UV-stabilised particles according to claim 7, wherein the pearlescent pigments, interference pigments, multilayered pigments and goniochromatic pigments are based on natural or synthetic mica, $Al_2O_3$, $TiO_2$, $SiO_2$, $Fe_2O_3$, glass or graphite platelets.

9. Process for the production of UV-stabilised particles according to claim 1, wherein one or more UV protection agents or UV stabilisers are either applied directly to the inorganic particle surface to be protected and immobilised with a polymer or polymer mixture applied subsequently or applied to the surface and immobilised irreversibly in one step in the form of a mixture with the polymer or polymers.

10. Process according to claim 9, wherein the polymer is an LCST and/or UCST polymer or polymer mixture of LCST and/or UCST polymers.

11. A surface coating, water-borne coating, powder coating, paint, printing ink, security printing ink, plastic, concrete, cosmetic, agricultural sheeting, tent awning, laser markable paper or plastic, or pigment composition comprising UV-stabilised particles according to claim 1.

12. A method for providing UV protection to a composition which comprises incorporating UV-stabilised particles according to claim 1 in the composition.

13. A composition comprising the UV-stabilised pigments according to claim 1.

14. UV-stabilised particles according to claim 1, wherein the inorganic particles are: $SiO_2$ beads which are uncoated or coated with one or more metal oxides; white pigments selected from titanium dioxide, zinc white, paint-grade zinc oxide, lead white, zinc sulfide or lithopone; black pigments selected from iron-manganese black, spinel black or iron oxide black pigments; color pigments selected from chromium oxide, chromium oxide hydrate green, chromium green, cobalt green, ultramarine green, cobalt blue, ultramarine blue, iron blue, manganese blue, ultramarine violet, cobalt and manganese violet, iron oxide red, cadmium sulfoselenide, molybdate red, ultramarine red, iron oxide brown, mixed brown, spinel and corundum phases, chromium orange, iron oxide yellow, nickel-titanium yellow, chromium-titanium yellow, cadmium-zinc sulfide, chromium yellow, zinc yellow, alkaline earth metal chromates, Naples yellow and bismuth vanadate; or magnetic pigments selected from $CrO_2$, $Fe_2O_3$, $Fe_3O_4$, Co-modified iron oxides, Ba ferrites, pure iron pigments and graphite platelets.

15. UV-stabilised particles according to claim 1, wherein the inorganic particles are BiOCl platelets.

16. UV-stabilised particles according to claim 1, wherein the inorganic particles are inorganic pigment particles.

* * * * *

UNITED STATES PATENT AND TRADEMARK OFFICE
CERTIFICATE OF CORRECTION

PATENT NO.       : 7,579,079 B2                                      Page 1 of 1
APPLICATION NO. : 10/518464
DATED            : August 25, 2009
INVENTOR(S)      : Adalbert Huber It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 347 days.

Signed and Sealed this

Fourteenth Day of September, 2010

David J. Kappos
*Director of the United States Patent and Trademark Office*